United States Patent [19]

Schröer et al.

[11] Patent Number: 5,194,641

[45] Date of Patent: Mar. 16, 1993

[54] METHOD OF MANUFACTURING NONIONIC SURFACTANTS LOW IN ALKYLENE OXIDES AND LOW IN 1,4-DIOXANE, USING ALKALI METAL ALKOXIDES AS CATALYSTS

[75] Inventors: Egbert Schröer, Dorsten; Klaus Schulze, Haltern; Ekkehard Wienhöfer, Marl, all of Fed. Rep. of Germany

[73] Assignee: Huels Aktiengesellschaft, Marl, Fed. Rep. of Germany

[21] Appl. No.: 697,423

[22] Filed: May 9, 1991

[51] Int. Cl.$^5$ .............................................. C07C 51/00
[52] U.S. Cl. ................................... 554/149; 554/148; 564/475

[58] Field of Search .................... 260/410.6; 554/149; 564/475

[56] References Cited

FOREIGN PATENT DOCUMENTS 408857  1/1991  European Pat. Off. .

*Primary Examiner*—Jose G. Dees
*Assistant Examiner*—Deborah D. Carr
*Attorney, Agent, or Firm*—Oblon, Spivak, McClelland, Maier & Neustadt

[57] ABSTRACT

Alkoxidation products are prepared from amines, fatty acids and oils, which are low in alkylene oxides and 1,4-dioxane by reacting an amine, fatty acid, ester or oil with an alkylene oxide in the presence of a catalyst of an alkali fatty alkoxide obtained by reaction of an alkali hydroxide with a fatty alcohol at elevated temperature.

14 Claims, No Drawings

METHOD OF MANUFACTURING NONIONIC SURFACTANTS LOW IN ALKYLENE OXIDES AND LOW IN 1,4-DIOXANE, USING ALKALI METAL ALKOXIDES AS CATALYSTS

BACKGROUND OF THE INVENTION

1. Field of the Invention

The present invention relates to a method of producing nonionic surfactants low in alkylene oxides and low in 1,4-dioxane, by a catalytic method employing an alkali metal fatty alkoxide and to a method of producing said alkali metal fatty alkoxide.

2. Description of the Background

Because products containing nonionic surfactants are used essentially on a daily basis, and in view of the possible toxicological hazard of appreciable impurities of alkylene oxides and 1,4-dioxane in these surfactants, it is necessary to have a supply of surfactant products having very low levels of alkylene oxides and 1,4-dioxane.

The customary production of nonionic surfactants employs catalysis with Na ions and/or K ions. These ions are added to the likes of such reactants as alkylphenols, fatty alcohols, glycols, amines, fatty acids, and oils. Preferably, the Na and/or K ions are added in the form of NaOH, KOH, sodium methoxide, or potassium methoxide. Water of solution and water of reaction are removed under an inert nitrogen atmosphere. Then the reaction with the alkylene oxide is carried out.

According to U.S. Pat. No. 4,453,023, barium alkoxide can also be used as a catalyst. Barium alkoxide is produced, according to the U.S. patent, by reaction of barium metal with ethanol, followed by reaction with, e.g., ethylhexanol. Vacuum distillation is used to remove ethanol from the barium ethylhexanoxide which is produced.

Eur. Pat. 0 026 547 describes a similar catalyst preparation procedure, according to which alkoxides of Ca, Sr, or Ba may be prepared by reacting Ca, Sr, or Ba metal with ethanol, followed by reaction with decanol. The regenerated ethanol is then removed by applying a vacuum to the reaction mixture.

There are several disadvantages associated with the method of producing nonionic surfactants as disclosed in U.S. Pat. No. 4,453,023, and with the use of catalysts in the production of nonionic surfactants, which catalysts are prepared by the two-step method in which an alkali metal is reacted with ethanol, followed by reaction of the metal ethoxide with a higher alcohol. These disadvantages entail very high costs, as well as high residual contents of alkylene oxides (c. 200 ppm) and 1,4-dioxane (c. 5000 ppm). Further, there are problems associated with the use of metals for producing alkoxides, because of the liberation of water. Further, the products produced with ethylhexanoxide catalysts have a strong odor of ethylhexanol.

Thus, a need continues to exist for a method of manufacturing nonionic ethoxylated surfactants low in alkylene oxides and low in 1,4-dioxane.

SUMMARY OF THE INVENTION

Accordingly, one object of the present invention is to provide a catalyst for the alkoxylation of fatty alkoxide of various compounds to produce nonionic surfactants.

Briefly, this object and other objects of the present invention as hereinafter will become more readily apparent can be attained in a method of preparing alkoxidation products from amines, fatty acids and oils (esters), which products are low in alkylene oxides and low in 1,4-dioxane by reacting an amine, fatty acid or oil with an alkylene oxide in the presence of a catalyst of an alkali fatty alkoxide obtained by reaction of an alkali hydroxide with a fatty alcohol at elevated temperature.

The discovery of the present invention is that surprisingly the alkylene oxide content in nonionic surfactants can be reduced to <10 ppm and the 1,4-dioxane content to <100 ppm, by the use of a catalyst produced according to the method of the present invention.

The preferred fatty alcohol for preparing the catalyst is isotridecanol. Polyols may be used which include ethylene glycol, propylene glycol, butylene glycol, pentylene glycol, hexylene glycol, heptylene glycol, neopentylene glycol, decylene glycol, diethylene glycol, triethylene glycol, dipropylene glycol, tripropylene glycol, pentaerythritol, galactitol, sorbitol, mannitol, erythritol, trimethylothethane and trimethylolpropane. Other useful alcohols are described in U.S. Pat. No. 4,453,023. Preferably this alcohol is reacted with KOH or NaOH at 100°-160° C., preferably 120°-140° C., normally in the absence of solvent. However it is possible to employ a lower alkanol solvent such as methanol or ethanol. A distinctive feature of the invention is that a solvent is not required.

The preferred reactants for the alkoxidation reaction with the fatty acid alcoholate include oils such as castor oil, coconut oil, and soybean oil; mixtures of $C_8-C_{24}$ mono- and diglycerides; $C_{12}-C_{22}$ fatty acids; and amines with 12-24 C atoms, preferably 12-18 C atoms. The alkoxidation is carried out at c. 140°-200° C., preferably 160°-90° C. and is normally conducted in the absence of solvent under an inert atmosphere.

The alkylene oxide reactant is the likes of ethylene oxide, propylene oxide, butylene oxide and the like. Preferred is ethylene oxide. The amount of alkylene oxide employed as a reactant is an amount sufficient to form a product containing the desired amount of reacting alkylene oxide units.

The amount of alkylene oxide which reacts with amine fatty acid or oil starting material is such that the following relative amounts of alkylene oxide to amine, fatty acid or oil reactant are employed: 1 to 50 moles of alkylene oxide, preferably 2 to 34 moles of alkylene oxide per mole of amine; 2 to 80 moles, preferably 3-20 moles of alkylene oxide per mole of fatty acid; and 4 to 90 moles, preferably 11-70 moles of alkylene oxide per mole of oil. In the alkoxidation reaction, the amount of catalyst which is present varies depending on the amount of amine, fatty acid or oil reactant employed. Thus, usually from 2 to 10 mmole of catalyst is employed per mole of amine, from 2 to 20 mmole of catalyst is employed per mole of fatty acid, and from 10 to 40 mmole of catalyst is employed per mole of oil.

Having generally described this invention, a further understanding can be obtained by reference to certain specific examples which are provided herein for purposes of illustration only and are not intended to be limiting unless otherwise specified.

EXAMPLE 1

Invention a) A 561 g amount of KOH (flake) and 2,029 g of isotridecanol were heated, with stirring, to 130° C. in a 5-liter glass reactor equipped with a heater, a stirrer, and a nitrogen inlet. Stirring was continued 48 hr at 130° C. The resulting alkoxide was pourable and pumpable at 70°-90° C.

b) A 561 g amount of 50% KOH and 1,014.5 g isotridecanol were mixed at 60° C. The resulting emulsion was brought to reaction at 130° C. under a nitrogen atmosphere, above a thin layer evaporator, with a dropping rate of 500 g/hr, wherewith water was removed. The resulting alkoxide was pourable and pumpable at 70°-90° C.

EXAMPLE 2

Invention a) Using the apparatus and conditions described in Example 1a, 400 g NaOH (flake) and 2,029 g isotridecanol were charged to the reactor. The reaction mixture was stirred 72 hr at 130° C. The water by-product was driven off with the aid of nitrogen. The resulting alkoxide was pourable and pumpable at 70°-90° C.

b) A sodium isotridecanoxide was produced using a thin layer evaporator, under the conditions of Example 1b, with a starting material of 800 g of 25% NaOH solution and 1,014.5 g isotridecanol. The isotridecanoxide was pourable and pumpable at 70°-90° C.

EXAMPLE 3

Invention

A 370 g (2 mol) amount of laurylamine was heated to 60° C. in a 5-liter glass reactor equipped with a heater, a stirrer, and a nitrogen inlet, with nitrogen purging, to provide an inert atmosphere. Then 176 g (4 mol) ethylene oxide was added at 160° C., under an initial nitrogen pressure of 0.5 bar and a maximum pressure of 3.5 bar. The reaction mixture was then cooled to 60° C., and 2.42 g (10.16 mmol) K isotridecanoxide was added. The mixture was stirred with nitrogen purging in order to maintain an inert atmosphere. Then 704 g (16 mol) ethylene oxide was added at 160° C., under an initial nitrogen pressure of 1.5 bar and a maximum pressure of 3 bar abs.

The residual content of ethylene oxide was <1 ppm, and that of 1,4-dioxane was 75 ppm.

EXAMPLE 4

Invention

A 566.7 g (2 mol) amount of oleic acid and 3.58 g (15.05 mmol) Na isotridecanoxide were heated to c. 60° C. in the apparatus and under the conditions of Example 3. The mixture was stirred with nitrogen purging to maintain an inert atmosphere. Then 616 g (14 mol) ethylene oxide was added at 180° C.

The residual content of ethylene oxide in the resulting product was 5 ppm, and that of 1,4-dioxane was 80 ppm.

EXAMPLE 5

Invention

A 936 g (1 mol) amount of castor oil and 8.16 g (34.27 mmol) Na isotridecanoxide were heated to c. 60° C. in the apparatus and under the conditions of Example 3. The mixture was stirred with nitrogen purging to maintain an inert atmosphere. Then 1,760 g (40 mol) ethylene oxide was added at 180° C.

The residual content of ethylene oxide in the resulting product was 6 ppm, and that of 1,4-dioxane was 80 ppm.

EXAMPLE 6

Comparison Example

As in Example 3, 370 g (2 mol) laurylamine was heated to c. 60° C. and was stirred with nitrogen purging to maintain an inert atmosphere. Then 176 g (4 mol) ethylene oxide was added at 160° C. The mixture was cooled to 60° C., and 10.16 mmol Ba ethylhexanoxide (prepared according to the method described in U.S. Pat. No. 4,453,023) was added, and the resulting mixture was stirred with nitrogen purging. Then 704 g (16 mol) ethylene oxide was added at 160° C.

The product had a strong odor of ethylhexanol.

The residual content of ethylene oxide was 120 ppm, and that of 1,4-dioxane was 890 ppm.

EXAMPLE 7

Comparison Example

As in Example 4, 566.7 g (2 mol) oleic acid and 15.05 mmol Ba decanoxide (prepared according to the method described in Eur. Pat. 0 026 547) were heated to c. 60° C. and were stirred with nitrogen purging. Then 616 g (14 mol) ethylene oxide was added at 180° C.

The residual content of ethylene oxide was 150 ppm, and that of 1,4-dioxane was 4,700 ppm.

EXAMPLE 8

Comparison Example

As in Example 5, 936 g (1 mol) castor oil and 34.27 mmol 25% NaOH were stirred together, and water was driven off by purging with nitrogen at 130° C. Then 1,760 g (40 mol) ethylene oxide was added at 180° C.

The residual content of ethylene oxide was 200 ppm, and that of 1,4-dioxane was 2,600 ppm.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of producing alkoxidation products from amines, fatty ac-ids, and oils, which products are low in alkylene oxides and low in 1,4-dioxane, comprising:
    reacting an amine, fatty acid or oil with an alkylene oxide in the presence of an alkali fatty alkoxide catalyst obtained by direct action of an alkali hydroxide with a fatty alcohol at elevated temperature in the absence of a solvent.

2. The method of claim 1, wherein said alkali hydroxide is sodium hydroxide or potassium hydroxide.

3. The method of claim 1, wherein said fatty alcohol is isotridecanol.

4. The method of claim 1, wherein the catalyst formation reaction is conducted at a temperature of 100°-60° C.

5. The method of claim 4, wherein said catalyst formation reaction is conducted at a temperature of 120°-140° C.

6. The method of claim 1, wherein said oil is castor oil, coconut oil, soybean oil or a $C_8$-$C_{24}$ mono- or di-glyceride; said fatty acid is a $C_{12}$-$C_{22}$ fatty acid and said amine contains from 12 to 24 carbon atoms.

7. The method of claim 1, wherein said alkoxidation reaction occurs at a temperature of 140°-200° C.

8. The method of claim 1, wherein from 1 to 50 moles of alkylene oxide are reacted with one mole of amine.

9. The method of claim 1, wherein from 2 to 80 moles of alkylene oxide are reacted with one mole of fatty acid.

10. The method of claim 1, wherein from 4 to 90 moles of alkylene oxide are reacted with one mole of oil.

11. The method of claim 1, wherein from 2 to 10 mmole of catalyst is employed per mole of amine.

12. The method of claim 1, wherein from 2 to 20 mmole of catalyst is employed per mole of fatty acid.

13. The method of claim 1 wherein from 10 to 40 mmole of catalyst is employed per mole of oil.

14. A method of producing alkoxidation products from amines, fatty acids, and oils, which products are low in alkylene oxides and low in 1,4-dioxane, comprising:
reacting an amine, fatty acid or oil with an alkylene oxide in amounts of from 1 to 50 moles, 2 to 80 mols or 4 to 90 mols of alkylene oxide per mol of amine, fatty acid or oil, respectively, at a temperature of 140°–200° C. in the presence of a catalyst of a fatty acid alkoxide employed in an amount of 2 to 10 mmole, 2 to 20 mmole or 10 to 40 mmole per mole of amine, fatty acid or oil, respectively, said catalyst obtained by reaction of an alkali hydroxide with a fatty alcohol at a temperature of 100°–160° C.

* * * * *

UNITED STATES PATENT AND TRADEMARK OFFICE
CERTIFICATE OF CORRECTION

PATENT NO. : 5,194,641
DATED : March 16, 1993
INVENTOR(S) : EGBERT SCHROER ET AL It is certified that error appears in the above-identified patent and that said Letters Patent is hereby corrected as shown below:

<u>COL.</u>  <u>LINE</u>

2,  33,  delete "160°-90°C" and insert --160°-190°C--;

4,  58 (Claim 4), delete "100°-60°C" and insert --100°-160°C--.

Signed and Sealed this

Eleventh Day of January, 1994

Attest:

BRUCE LEHMAN

Attesting Officer   Commissioner of Patents and Trademarks